(12) United States Patent
Kurkowski et al.

(10) Patent No.: US 9,242,017 B2
(45) Date of Patent: Jan. 26, 2016

(54) SYSTEM AND METHOD TO ELECTRONICALLY DETERMINE ADEQUATE GAMMA RADIATION STERILIZATION TIME

(71) Applicant: Maxim Integrated Products, Inc., San Jose, CA (US)

(72) Inventors: Hal Kurkowski, Dallas, TX (US); Subbayya Chowdary Yanamadala, Frisco, TX (US); Prem Ramachandran Nayar, Frisco, TX (US); James Price Cusey, Dallas, TX (US); Shiauchwun G. Pwu, Frisco, TX (US); John Wettroth, Cary, NC (US)

(73) Assignee: Maxim Integrated Products, Inc., San Jose, CA (US)

( * ) Notice: Subject to any disclaimer, the term of this patent is extended or adjusted under 35 U.S.C. 154(b) by 288 days.

(21) Appl. No.: 13/927,526

(22) Filed: Jun. 26, 2013

(65) Prior Publication Data

US 2014/0264039 A1   Sep. 18, 2014

Related U.S. Application Data

(60) Provisional application No. 61/787,245, filed on Mar. 15, 2013.

(51) Int. Cl.
 *A61L 2/08*  (2006.01)
 *A61L 2/28*  (2006.01)

(52) U.S. Cl.
 CPC . *A61L 2/08* (2013.01); *A61L 2/081* (2013.01); *A61L 2/28* (2013.01)

(58) Field of Classification Search
 CPC .............. A61L 2/08; A61L 2/081; A61L 2/28
 See application file for complete search history.

(56) References Cited

U.S. PATENT DOCUMENTS

| | | | |
|---|---|---|---|
| 8,575,560 B1 * | 11/2013 | Fechner | 250/370.14 |
| 2011/0273272 A1 * | 11/2011 | Burke | 340/10.1 |
| 2013/0341521 A1 * | 12/2013 | Fechner | 250/370.14 |
| 2013/0341522 A1 * | 12/2013 | Fechner | 250/370.14 |

\* cited by examiner

*Primary Examiner* — Mark R Gaworecki (57) ABSTRACT

An integrated circuit includes a sensing module, a measuring module, a comparing module, and memory. The sensing module senses radiation incident on the integrated circuit. The measuring module communicates with the sensing module and measures an amount of the radiation incident on the integrated circuit. The comparing module communicates with the measuring module and compares the amount of the radiation to a predetermined threshold and generates an indication that the amount of the radiation is less than the predetermined threshold or that the amount of the radiation is greater than or equal to the predetermined threshold. The memory stores the indication.

11 Claims, 5 Drawing Sheets

SYSTEM AND METHOD TO ELECTRONICALLY DETERMINE ADEQUATE GAMMA RADIATION STERILIZATION TIME

CROSS-REFERENCE TO RELATED APPLICATIONS

This application claims the benefit of U.S. Provisional Application No. 61/787,245, filed on Mar. 15, 2013. The entire disclosure of the application referenced above is incorporated herein by reference.

FIELD

The present disclosure relates generally to sensing radiation and more specifically to systems and methods for electronically determining whether a medical device is sterilized with adequate radiation.

BACKGROUND

The background description provided here is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Medical products can be sterilized in many ways. For example, the medical products can be heated in an autoclave (e.g., using steam at temperatures above 125 degrees Celsius and at pressures of about two atmospheres). Alternatively, the medical products can be treated chemically (e.g., using ethylene oxide). Alternatively, the medical products can be irradiated (e.g., using gamma rays having radiation levels of 2-7 Mrad or 20-70 KGray).

Medical instruments are typically considered properly sterilized when a minimum amount of radiation is absorbed by the instruments. To ensure that each instrument on a pallet receives the minimum amount of radiation for proper sterilization, manufacturers often over-irradiate the instruments. Over-irradiating can be expensive and time-consuming. Further, radiation results cannot be stored in nonvolatile memories based on floating-gate technologies (e.g., EPROM, EEPROM, and flash memories) since these memories are erased by the high levels of radiation required to sterilize medical instruments.

SUMMARY

An integrated circuit comprises a sensing module, a measuring module, a comparing module, and a memory. The sensing module senses radiation incident on the integrated circuit. The measuring module communicates with the sensing module and measures an amount of radiation incident on the integrated circuit. The comparing module communicates with the measuring module and compares the amount of the radiation to a predetermined threshold and generates an indication that the amount of the radiation is less than the predetermined threshold or that the amount of the radiation is greater than or equal to the predetermined threshold.

In other features, the radiation includes an ionizing radiation, and the integrated circuit further comprises a medical device that receives the radiation.

In other features, the integrated circuit further comprises an output module that outputs the indication to a system external to the integrated circuit, where the indication indicates whether the medical device is sterilized.

In other features, the integrated circuit further comprises an output module that outputs the indication to a system generating the radiation, where the system stops generating the radiation based on the indication.

In other features, the integrated circuit further comprises a periodic activation module that activates the sensing module and the measuring module at predetermined time intervals, and an output module that outputs the amount of the radiation measured by the measuring module to an internal memory or a system with external memory that logs the amount of the radiation measured at the predetermined time intervals.

In other features, the sensing module includes a first oscillator having a first period that changes substantially due to the radiation and a second oscillator having a second period that does not change substantially due to the radiation. The measuring module measures the amount of the radiation based on a ratio of the first and second periods after the first and second oscillators are exposed to the radiation.

In other features, the sensing module includes a MOSFET having a threshold voltage that shifts due to the radiation. The measuring module measures the amount of the radiation based on an amount of shift in the threshold voltage of the MOSFET due to the radiation.

In still other features, a method comprises sensing radiation incident on an integrated circuit using a sensing element integrated in the integrated circuit, and measuring an amount of the radiation incident on the integrated circuit in response to sensing the radiation incident on the integrated circuit using the sensing element integrated in the integrated circuit. The method further comprises comparing the measured amount of the radiation to a predetermined threshold, and generating an indication that the measured amount of the radiation is less than the predetermined threshold or that the amount of radiation is greater than or equal to the predetermined threshold.

In other features, the radiation includes an ionizing radiation, and the method further comprises outputting the indication to a system external to the integrated circuit, and determining based on the indication whether a medical device integrated in the integrated circuit is sterilized.

In other features, the method further comprises outputting the indication to a system external to the integrated circuit, and determining based on the indication whether to continue or stop generating the radiation.

In other features, the method further comprises measuring the radiation at predetermined time intervals, and logging the amount of the radiation measured at the predetermined time intervals.

In other features, the sensing element comprises first and second oscillators respectively having first and second periods, and the method further comprises measuring the amount of the radiation based on a ratio of the first and second periods after the first and second oscillators are exposed to the radiation. The first period of the first oscillator changes substantially due to the radiation. The second period of the second oscillator does not change substantially due to the radiation.

In other features, the sensing element includes a MOSFET whose threshold voltage shifts due to the radiation, and the method further comprises measuring the amount of the radiation based on an amount of shift in the threshold voltage of the MOSFET after exposure to the radiation.

Further areas of applicability of the present disclosure will become apparent from the detailed description, the claims and the drawings. The detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings, wherein.

In the drawings, reference numbers may be reused to identify similar and/or identical elements.

DETAILED DESCRIPTION

The present disclosure relates to an integrated circuit (IC) that is mounted on an object to be irradiated, that measures an amount of radiation received by the object, that compares the amount of received radiation to a predetermined minimum amount sufficient to sterilize the object, and that generates an indication based on the comparison to indicate whether the object is properly sterilized. The indication can be stored in a one-time programmable (OTP) memory in the IC, where the OTP memory is capable of withstanding the radiation. The indication can be read by an end user (e.g., a surgical caregiver) to determine whether an instrument has been properly sterilized. The indication can also be used by the manufacturer (e.g., in real time) to optimize irradiation procedures. For example, based on the indication, the manufacturer can determine whether to continue or stop irradiation, whether to change duration and/or strength of radiation, and so on. The IC can provide the measurement of the amount of radiation in analog and/or digital form. Further, the IC can periodically measure radiation levels that the object is exposed to and log the radiation levels. Alternatively, the IC can output the measured radiation levels periodically to a logging device that generates a chronological record of radiation exposure.

Figure 1A:
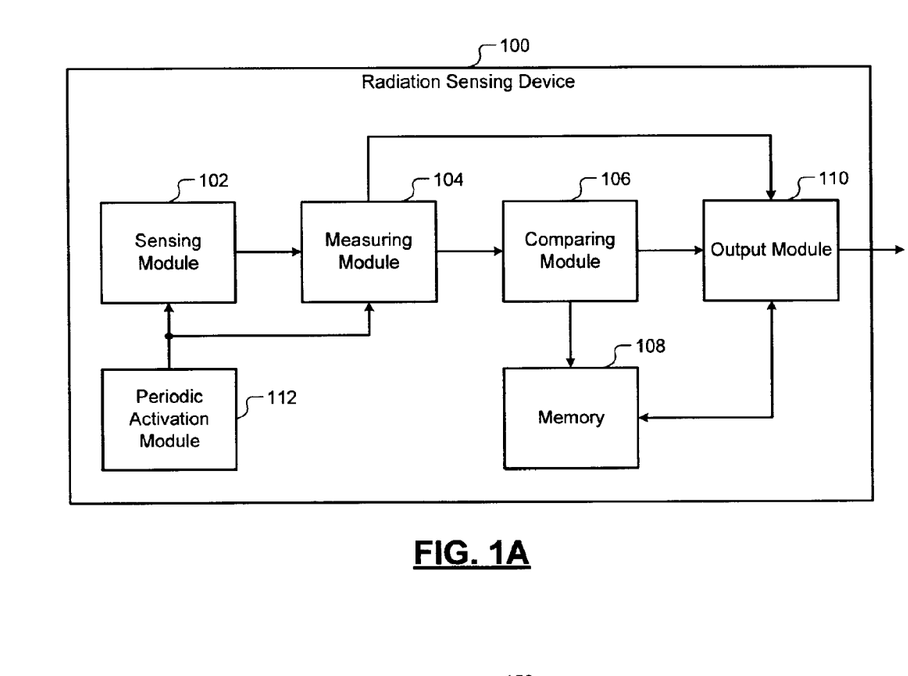
FIG. 1A is a functional block diagram of a radiation sensing device according to the present disclosure.
Figure 1B:
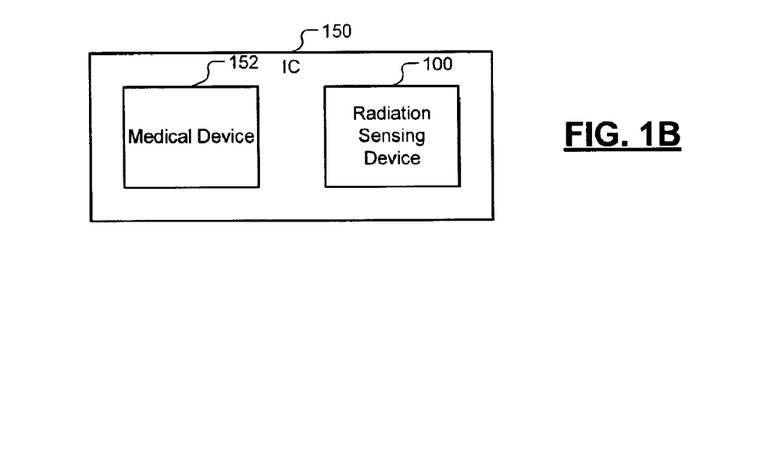
FIG. 1B is a functional block diagram of an integrated circuit comprising the radiation sensing device of FIG. 1A and a medical device according to the present disclosure.

Referring now to FIGS. 1A and 1B, a radiation sensing device 100 according to the present disclosure is shown. In FIG. 1A, the radiation sensing device 100 includes a sensing module 102, a measuring module 104, a comparing module 106, a memory 108, an output module 110, and a periodic activation module 112. The memory 108 is an OTP memory that is capable of withstanding radiation. For example, the memory is capable of storing data in presence of gamma ray radiation having radiation levels of 2-7 Mrad or 20-70 KGray. In some implementations, the radiation sensing device 100 can be implemented as an IC. Throughout the present disclosure, gamma-ray radiation is used as an example only. Any other ionizing radiation may be used instead.

In FIG. 1B, an IC 150 including a medical device 152 and the radiation sensing device 100 is shown as an example implementation of the radiation sensing device 100. In some implementations, the medical device 152 and the radiation sensing device 100 may share some of the circuitry (e.g., the memory 108).

The sensing module 102 senses the radiation incident on the radiation sensing device 100. When the radiation sensing device 100 is integrated with the medical device 152, the sensing module 102 senses the radiation received by the medical device 152. The measuring module 104 measures the amount of radiation incident on the radiation sensing device 100. When the radiation sensing device 100 is integrated with the medical device 152, the measuring module 104 measures the amount of radiation received by the medical device 152.

In some implementations, the measuring module 104 may measure the amount of radiation received and generate an analog or digital representation of the amount of radiation received. The measuring module 104 may optionally store the analog or the digital representation of the amount of radiation received in the memory 108.

The comparing module 106 compares the amount of radiation to a predetermined threshold (e.g., a minimum amount of radiation adequate to properly sterilize the medical device 152). Based on the comparison, the comparing module 106 generates an indication (e.g., a quality control or QC bit). The indication may indicate that the amount of radiation received is less than the predetermined threshold (e.g., the QC bit is reset) or that the amount of radiation received is greater than or equal to the predetermined threshold (e.g., the QC bit is set). The memory 108 can optionally store the indication (i.e., the QC bit).

In some applications, the irradiation occurs when there is no power applied to the IC 150. Therefore, the radiation sensing device 100 cannot measure or store anything until the IC 150 is powered up later. When the medical device 152 is finally put into use (i.e., powered up), the radiation sensing device 100 generates an output (i.e., the QC bit) based on the radiation exposure. The radiation sensing device 100 can optionally store the QC bit in the memory 108 at that time. Alternatively, the radiation sensing device 100 can generate the QC bit in real time, as needed, and store the QC bit in a register (e.g., in a volatile memory) in the radiation sensing device 100.

For example, when an end user is ready to use the medical device 152, the medical device 152 may be connected to a system (not shown) that controls, verifies, and/or operates the medical device 152. The connection may be wired or wireless. The radiation sensing device 100 powers up using power received from the system and generates the QC bit based on the radiation exposure. The QC bit may be optionally stored in the memory 108 or may be stored in a register in the radiation sensing device 100. The system can check the QC bit to determine whether the medical device 152 was properly sterilized. The output module 110 outputs the QC bit to the system via the wired or wireless connection. The system may approve using the medical device 152 if the QC bit indicates that the medical device 152 was properly sterilized (e.g., if the QC bit is set). The system may reject the medical device 152 if the QC bit indicates that the medical device 152 was not properly sterilized (e.g., if the QC bit is reset).

The output module 110 can also output the indication to a system that generates the radiation (system not shown). The system can stop generating the radiation (i.e., irradiating the medical device 152) if the system determines based on the indication that the medical device 152 received the minimum amount of radiation adequate to properly sterilize the medical device 152. The output module 110 can also periodically output the analog or the digital representation of the amount of radiation measured by the measuring module 104 to a system (not shown) that can generate a chronological record of radiation incident on the radiation sensing device 100.

Specifically, the periodic activation module 112 can periodically activate the radiation sensing device 100. For example, the periodic activation module 112 can activate the sensing module 102 and the measuring module 104 at predetermined time intervals. When activated, the sensing module 102 can sense the radiation received by the radiation sensing device 100. The measuring module 104 can measure the amount of radiation received by the radiation sensing device 100. The output module 110 can output the analog or the digital representation of the amount of radiation measured by the measuring module 104 to a system (not shown) that logs the amount of radiation measured at the predetermined time intervals. The system can generate a chronological record of radiation incident on the radiation sensing device 100. Alternatively, the amount of radiation measured by the measuring module 104 can be stored in the memory 108 for retrieval by the system at a later time (e.g., periodically).

Figure 2A:
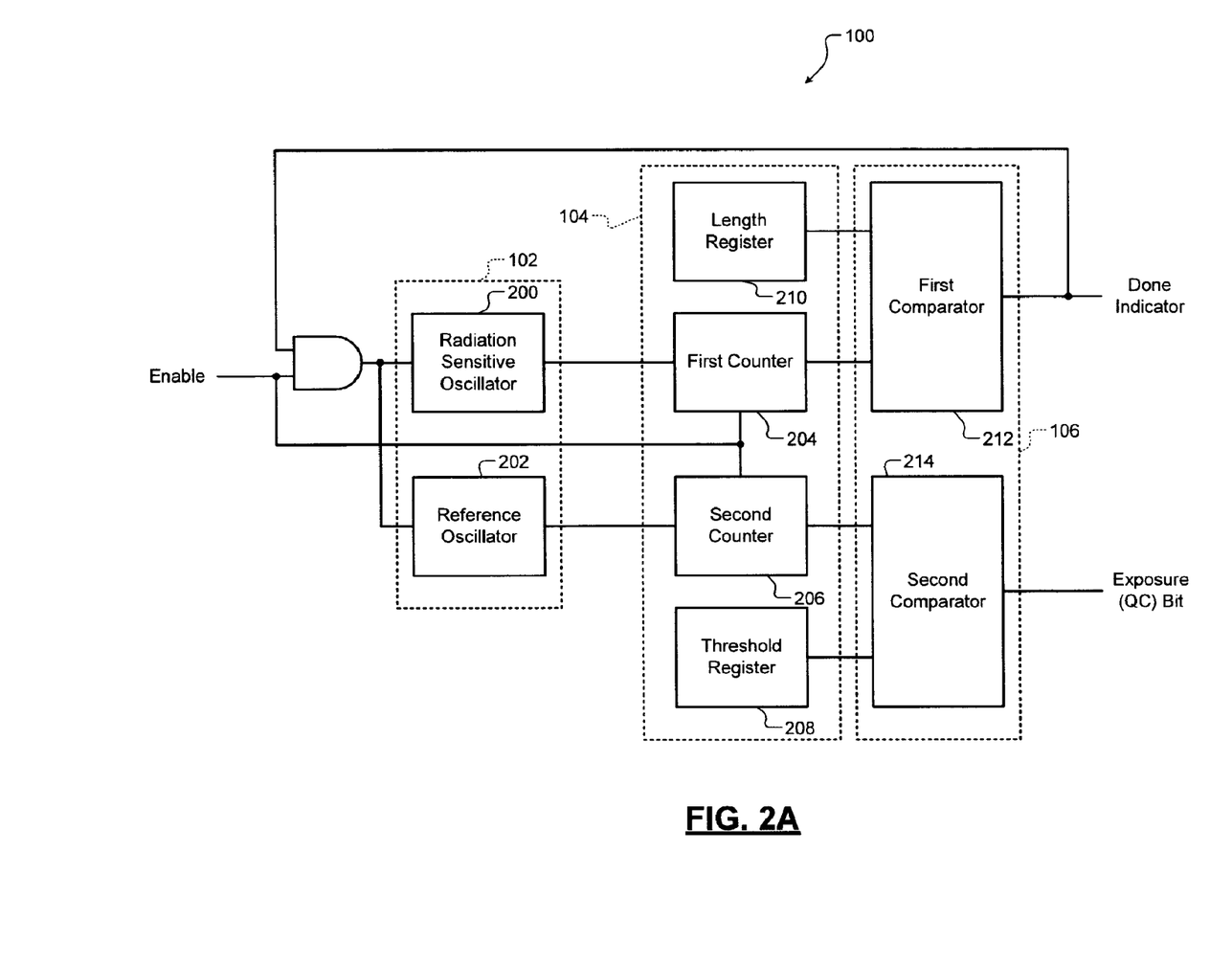
FIG. 2A is a functional block diagram of a first example implementation of the radiation sensing device according to the present disclosure.
Figure 2B:
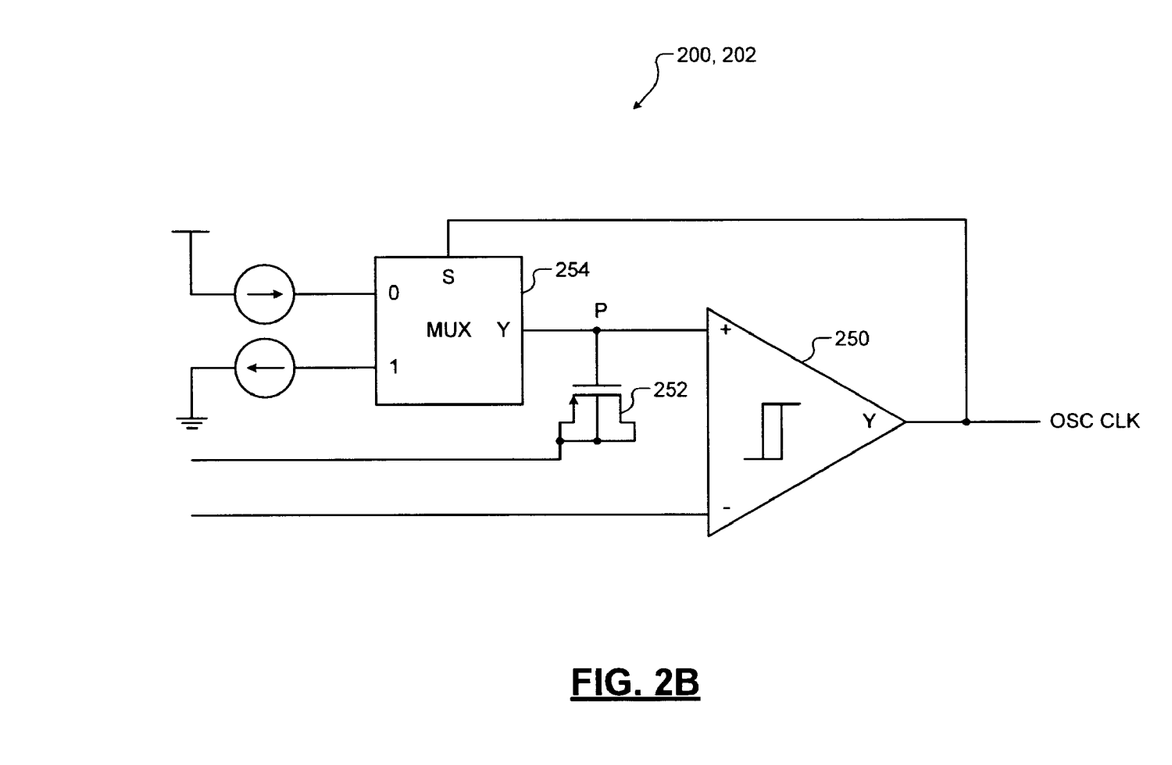
FIG. 2B is a schematic of an oscillator using a MOSFET as a radiation-sensing element according to the present disclosure.

Referring now to FIGS. 2A and 2B, a first example implementation of the radiation sensing device 100 is shown. In FIG. 2A, only the sensing module 102, the measuring module 104, and the comparing module 106 of the radiation sensing device 100 are shown for simplicity. The sensing module 104 includes a radiation sensitive oscillator 200 and a reference oscillator 202. The measuring module 104 includes a first counter 204, a second counter 206, a threshold register 208, and a length register 210. The comparing module 106 includes a first comparator 212 and a second comparator 214.

A period of the radiation sensitive oscillator 200 is less than a period of the reference oscillator 202 when not irradiated and is increased by exposure to radiation. The period of the reference oscillator 202 is largely unaffected by exposure to radiation as explained below.

The first and second counters 204, 206 are cleared to zero when the radiation sensing device 100 is disabled. When the radiation sensing device 100 is enabled, the first and second counters 204, 206 are respectively incremented once per period of the radiation sensitive oscillator 200 and the reference oscillator 202.

The length register 210 stores a number of periods of the radiation sensitive oscillator 200 after which both radiation sensitive oscillator 200 and reference oscillator 202 are stopped and both first and second counters 204, 206 are inhibited from counting further.

The second comparator 214 determines whether a final value of the second counter 206 is greater than or equal to a predetermined threshold value stored in the threshold register 208. If the final value of the second counter 206 is greater than or equal to a predetermined threshold value, the output of the second comparator 214, the exposure bit (i.e., the QC bit), is set to an active state. If the final value of the second counter 206 is less than the predetermined threshold value, the exposure bit (i.e., the QC bit) is set to an inactive state.

If the period of the radiation sensitive oscillator 200 is $T_{RV}$, the period of the reference oscillator 204 is $T_{REF}$, and the value stored in the length register 210 is N, then the value X locked into the second counter 206 after N periods of radiation sensitive oscillator 200 is given by:

$$X = N * \frac{T_{RV}}{T_{REF}} \quad \text{Equation (1)}$$

As explained below, the value of X can be used to indicate whether or not the radiation sensing device 100 has been exposed to a predetermined amount of radiation.

In FIG. 2B, an example implementation of the radiation sensitive oscillator 200 and the reference oscillator 202 is shown. Each of the radiation sensitive oscillator 200 and the reference oscillator 202 includes a comparator 250, a sensing element 252, and a multiplexer 254. For example only, the sensing element 252 may include a P-channel MOSFET. Other suitable devices capable of sensing radiation may be used as the sensing element 252 instead. The comparator 250 may have hysteresis of about $V_{HY}$=100 mV that is independent of a threshold voltage $V_{TS}$ of the sensing element 252.

When the output of the comparator 250 is b0, the multiplexer 254 sources current onto a capacitive node P until a voltage at the capacitive node P reaches a high trip point (a first predetermined threshold) of the comparator 250. At that time the output of the comparator 250 toggles to b1, and the multiplexer 254 begins to sink current from the capacitive node P and continues to do so until the voltage at the capacitive node P reaches a low trip point (a second predetermined threshold) of the comparator 250. At that time the output of the comparator 250 toggles back to b0, and the multiplexer 254 returns to sourcing current onto the capacitive node P.

The period of the resulting oscillations is given as follows, where C is the capacitance at the capacitive node P, and $I_{OSC}$ is the current through the source and sink.

$$\tau = \frac{2CV_{HY}}{I_{OSC}} \quad \text{Equation (2)}$$

Since the voltage swing at the capacitive node P centered about the reference voltage is relatively small, C can be approximated by the value of the $C_G$-vs.-$V_G$ characteristic of the P-channel MOSFET at $V_{GB}$, which is approximately equal to a difference between the two reference voltages.

In the reference oscillator 202, the P-channel MOSFET is biased such that, prior to irradiation, the P-channel MOSFET operates in accumulation region (i.e., with gate-to-body or applied voltage $V_{GB}$>>flatband voltage $V_{FB}$) so that $C=C_{ox}*W*L$, where $C_{ox}$ is capacitance in accumulation.

In the radiation sensitive oscillator 200, the P-channel MOSFET is biased such that, prior to irradiation, the P-channel MOSFET operates in depletion (i.e., with $V_{GB}$=0) so that $C<<C_{ox}*W*L$. Therefore, assuming that $V_{HY}$ and $I_{OSC}$ are equal between the two oscillators (i.e., the radiation sensitive oscillator 200 and the reference oscillator 202) and that the two P-channel MOSFETs have equal W and L values, equation (2) above indicates that $T_{RV}<<T_{REF}$ prior to irradiation. That is, prior to radiation, the period of the radiation sensitive oscillator 200 is much less than the period of the reference oscillator 202.

Exposure to radiation causes holes to be trapped in the gate oxide of the P-channel MOSFET and either electrons or holes (depending on surface potential) to be trapped at an interface between the gate oxide and the silicon surface of the P-channel MOSFETs. For the P-channel MOSFET in the radiation sensitive oscillator 200 operating in depletion with $V_{GB}$=0, the surface potential is such that holes rather than electrons are trapped at the interface between the gate oxide and the silicon surface. Accordingly, both the oxide traps and the interface traps drive the threshold voltage of the P-channel MOSFET more negative. This pushes the operation of the P-channel MOSFET closer to flat-band and therefore increases C, which in turn increases $T_{RV}$ from their pre-irradiation values. For the P-channel MOSFET in the reference oscillator 202, the change in the threshold voltage of the P-channel MOSFET only pushes the operation of the P-channel MOSFET further into accumulation and therefore does not appreciably change C or $T_{REF}$.

Since exposure to radiation increases $T_{RV}$ but not $T_{REF}$, the value of X in equation (1) above increases from its pre-irradiation value. Therefore, the value of X can be used to indicate whether the radiation sensing device 100 has been exposed to radiation.

In some applications (e.g., medical instruments) using the first example implementation, the radiation sensing device 100 may not be powered up when irradiation occurs. The radiation changes the threshold voltage of the sensing element 252 (e.g., P-channel MOSFET 252 in FIG. 2B) in each of the radiation sensitive oscillator 200 and the reference oscillator 202. The result of the change (i.e., different periods of the two oscillators 200, 202), however, cannot be observed until power is applied to the radiation sensing device 100 after irradiation. Subsequently, when the radiation sensing device 100 is powered up, the P-channel MOSFET in the radiation sensitive oscillator 200 is biased differently than in the reference oscillator 202. Thus, the radiation alters the operating characteristics (i.e., the threshold voltages) of the two sensing elements 252 in the two oscillators 200, 202. Subsequently, the two sensing elements 252 are biased differently so that the two sensing elements 252 operate differently, and the two oscillators 200, 202 produce different results (i.e., different periods) when power is applied.

Specifically, the P-channel MOSFET in the radiation sensitive oscillator 200 is biased so that it is in depletion. The capacitance at the capacitive node P in the radiation sensitive oscillator 200 is therefore initially much less than that in the reference oscillator 202. After radiation, the threshold voltage of the P-channel MOSFET in the radiation sensitive oscillator 200 moves from depletion to flat-band/accumulation. Thus the capacitance at the capacitive node P in the radiation sensitive oscillator 200 increases. The P-channel MOSFET in the reference oscillator 202 is biased so that it is in accumulation. The radiation drives the threshold voltage of the P-channel MOSFET in the reference oscillator 202 to an even more negative value. The capacitance at the capacitive node P in the reference oscillator 202, however, does not change much. Accordingly, the periods of the two oscillators 200, 202 differ due to a combination of radiation-induced change in the threshold voltage of the sensing elements 252 and the different biasing of the sensing elements 252.

Figure 3A:
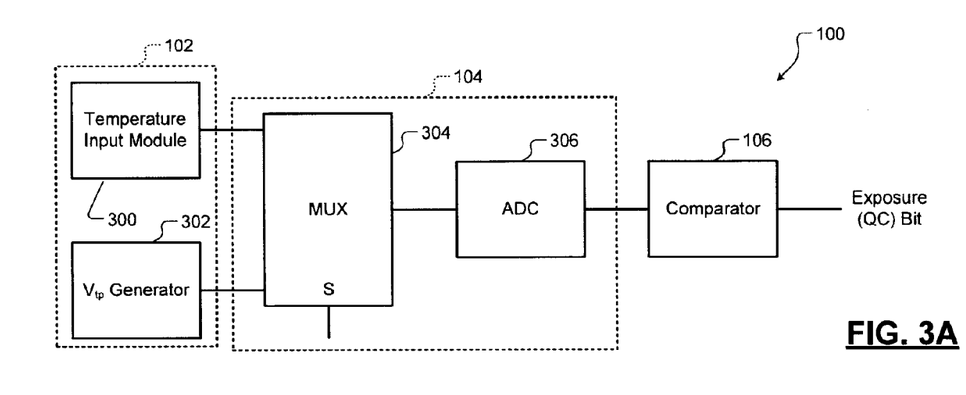
FIG. 3A is a functional block diagram of a second example implementation of the radiation sensing device according to the present disclosure.
Figure 3B:
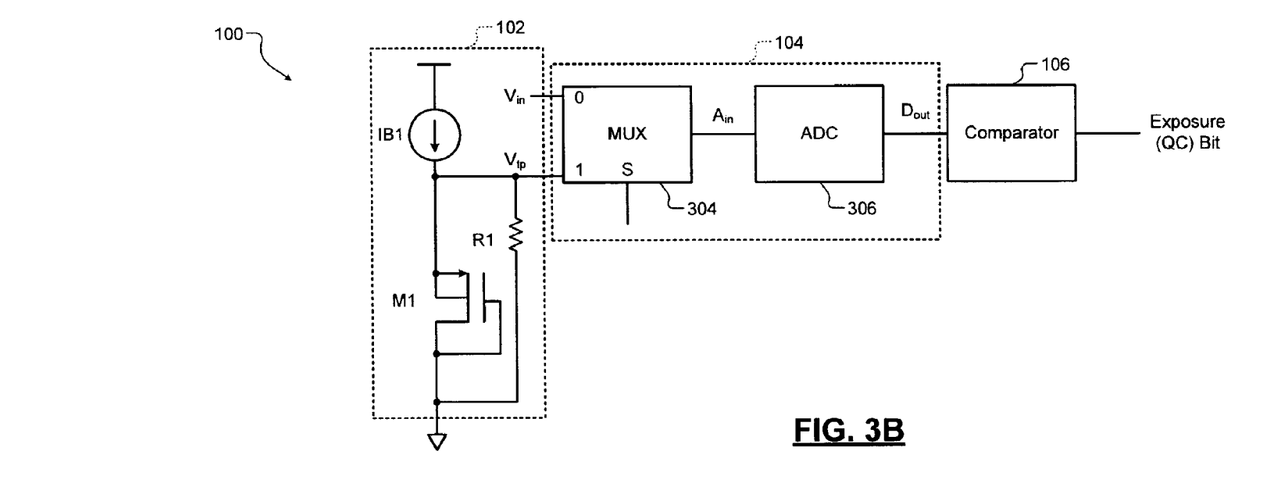
FIG. 3B is a schematic of the radiation sensing device of FIG. 3A showing a MOSFET used as a radiation-sensing element according to the present disclosure.

Referring now to FIGS. 3A and 3B, a second example implementation of the radiation sensing device 100 is shown. In FIG. 3A, only the sensing module 102, the measuring module 104, and the comparing module 106 of the radiation sensing device 100 are shown for simplicity. The sensing module 102 includes a temperature input module 300 and a threshold voltage generator 302. The measuring module 104 includes a multiplexer 304 and an ADC 306. The comparing module 106 includes a comparator.

The temperature input module 300 generates a voltage Vin corresponding to the ambient temperature (i.e., the temperature surrounding the radiation sensing device 100). For example, the temperature input module 300 may include a temperature transducer or a temperature-to-voltage converter. The threshold voltage generator 302 is shown in greater detail in FIG. 3B.

In FIG. 3B, the radiation sensing device 100 implemented as a data converter dosimeter is shown. When S=0, the ADC 306 converts the temperature input $V_{in}$ to a digital output $D_{out}$. When S=1, the multiplexer 304 selects a radiation sensitive input $V_{tp}$. The ADC 306 converts $V_{tp}$, which shifts after irradiation, to its digital representation $D_{out}$. $V_{tp}$ is generated by driving a current source IB1 to a diode-connected P-channel MOSFET M1. For M1, $V_{tp}=V_{SG1}$.

A calibration is performed before irradiation. During calibration, the select input S of the multiplexer 304 is initially set to 0, and the multiplexer 304 selects $V_{in}$. Therefore, $A_{in}=V_{in}$. $V_{in}$ is the PTAT (Proportional to Absolute Temperature) input. $D_{out}=T_1$, which is a digital representation of the temperature input.

Then the select input S of the multiplexer 304 is set to 1, and the multiplexer 304 selects $V_{tp}$. Therefore, $A_{in}=V_{tp}$. $V_{tp}$ is the $V_{SG1}$ of M1. Dout=$V_{tp}(T_1)=V_1$, where $V_1$ is $V_{SG1}$ voltage at temperature=$T_1$.

$V_{tp}(T_{ref})=V_1+a_1*\Delta T_1$ is stored in memory, where $V_{tp}(T_{ref})$ is $V_{SG1}$ voltage at temperature=$T_{ref}$ (e.g., 25° C.), $a_1$=temperature coefficient of $V_{tp}$, and $\Delta T_1$=T1−25° C. At this point, calibration is complete, and the radiation sensing device 100 is ready for irradiation.

Subsequently, after the radiation sensing device 100 is irradiated, the select input S of the multiplexer 304 is set to 0. The multiplexer 304 selects $V_{in}$. Therefore, $A_{in}=V_{in}$. $D_{out}=T_2$, which is a digital representation of the temperature input after irradiation. Then the select input S of the multiplexer 304 is set to 1. The multiplexer 304 selects $V_{tp}$. Therefore, $A_{in}=V_{tp}$, where $V_{tp}$ is the $V_{SG1}$ of M1. $D_{out}=V_{tp}(T_2)=V_2$, where $V_2$ is $V_{SG1}$ of M1 at temperature=$T_2$.

The shift in the threshold voltage $V_{tp}$ of M1 due to the irradiation is given by $$\Delta V_{tp}=V_2+a_1*\Delta T_2-V_{tp}(T_{ref})=(V_2-V_1)+a_1*(T_2-T_1) \quad \text{Equation (3)}$$

where $V_2+a_1*\Delta T_2$ is $V_{SG1}$ of M1 after irradiation at temperature=$T_{ref}$ (e.g., 25° C.); and $\Delta T_2=T_2-T_{ref}$. Alternatively, the shift in the threshold voltage $V_{tp}$ of M1 due to the irradiation can also be given by $$\Delta V_{tp}=V_2+a_1*\Delta T_2-V_{tp}(T_{ref})=(V_2-V_1)+a_1*(\Delta T_2-\Delta T_1) \quad \text{Equation (3.1)}$$

where $\Delta T_2=T_2-T_{ref}$.

From equation 3, $\Delta V_{tp}$ is proportional to $(V_2-V_1)$. Accordingly, $\Delta V_p$ is independent of the process. $\Delta V_{tp}$ is also temperature independent since $\Delta V_{tp}$ is proportional to $(T_2-T_1)$ term. A dosage indication, the QC bit, can be determined by comparing $\Delta V_{tp}$ to one or multiple pre-programmed digital trip points (predetermined thresholds) which represent the $V_{tp}$ shift after exposure. The comparing module 106 compares $\Delta V_{tp}$ to one or multiple pre-programmed digital trip points which represent the $V_{tp}$ shift after exposure to generate the dosage indication, the QC bit.

As explained with reference to the first example implementation, in the second example implementation, the radiation alters the operating characteristics (i.e., the threshold voltage) of the sensing element (M1 in FIG. 3B). Specifically, $V_{tp}$ increases due to irradiation and has a higher value when power is later applied after irradiation than during calibration. Accordingly, M1 operates differently than during calibration (performed before irradiation) when power is later applied after irradiation and produces results that are different due to irradiation than during calibration.

Figure 4:
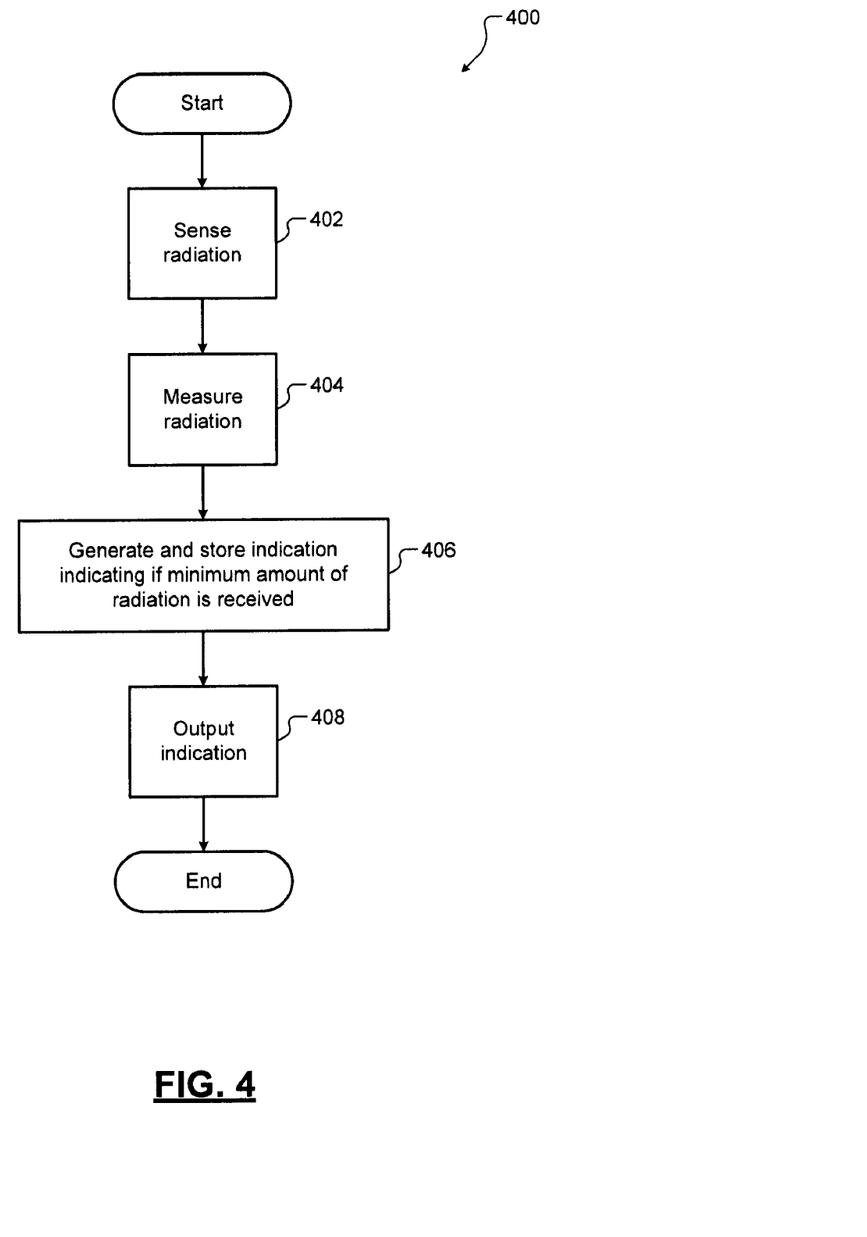
FIG. 4 is a flowchart of a method for sensing and measuring radiation according to the present disclosure.

Referring now to FIG. 4, a method 400 for sensing and measuring radiation according to the present disclosure is shown. For example, the method 400 can be used to sense and measure the amount of radiation received by a medical device that is integrated with a radiation sensing device in an integrated circuit according to the present disclosure.

At 402, control senses radiation incident on the integrated circuit using a sensing element integrated in the integrated circuit. In some implementations, the sensing element may include two oscillators, where the period of a first oscillator changes due to the radiation while the period of a second oscillator does not change due to the radiation. In some implementations, the sensing element may include a MOSFET whose threshold voltage changes due to the radiation.

At 404, control measures the amount of radiation received by the integrated circuit. For example, when the sensing element includes two oscillators, the amount of received radiation can be measured in terms of a ratio of the periods of the two oscillators after the radiation is received. Alternatively, if the sensing element includes a MOSFET, the amount of received radiation can be measured based on the amount of change in the threshold voltage of the MOSFET due to the radiation.

At 406, control generates and optionally stores an indication that indicates whether a minimum amount of radiation is received. In some implementations, control may also generate and optionally store an analog or a digital representation of the amount of radiation received. At 408, control outputs the indication to a system. In some implementations, the system may control the irradiation procedure based on the indication. In some implementations, the system may determine based on the indication whether the medical device was properly sterilized.

In some implementations, control can periodically measure the amount of radiation received by the integrated circuit and can output the amount of radiation received to a system. Based on the output received, the system can generate a log or a chronological record of radiation received by the integrated circuit over a period of time.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. As used herein, the phrase at least one of A, B, and C should be construed to mean a logical (A or B or C), using a non-exclusive logical OR. It should be understood that one or more steps within a method may be executed in different order (or concurrently) without altering the principles of the present disclosure.

In this application, including the definitions below, the term module may be replaced with the term circuit. The term module may refer to, be part of, or include an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor (shared, dedicated, or group) that executes code; memory (shared, dedicated, or group) that stores code executed by a processor; other suitable hardware components that provide the described functionality; or a combination of some or all of the above, such as in a system-on-chip.

The term code, as used above, may include software, firmware, and/or microcode, and may refer to programs, routines, functions, classes, and/or objects. The term shared processor encompasses a single processor that executes some or all code from multiple modules. The term group processor encompasses a processor that, in combination with additional processors, executes some or all code from one or more modules. The term shared memory encompasses a single memory that stores some or all code from multiple modules. The term group memory encompasses a memory that, in combination with additional memories, stores some or all code from one or more modules. The term memory may be a subset of the term computer-readable medium. The term computer-readable medium does not encompass transitory electrical and electromagnetic signals propagating through a medium, and may therefore be considered tangible and non-transitory. Non-limiting examples of a non-transitory tangible computer readable medium include nonvolatile memory, volatile memory, magnetic storage, and optical storage.

The apparatuses and methods described in this application may be partially or fully implemented by one or more computer programs executed by one or more processors. The computer programs include processor-executable instructions that are stored on at least one non-transitory tangible computer readable medium. The computer programs may also include and/or rely on stored data.

What is claimed is:

1. An integrated circuit comprising:
    a sensing module that senses radiation incident on the integrated circuit, wherein the sensing module includes a MOSFET having threshold voltage that shifts due to the radiation;
    a measuring module that communicates with the sensing module and that measures an amount of the radiation incident on the integrated circuit based on an amount of shift in the threshold voltage of the MOSFET due to the radiation; and
    a comparing module that communicates with the measuring module and that compares the amount of the radiation to a predetermined threshold and that generates an indication that the amount of the radiation is less than the predetermined threshold or that the amount of the radiation is greater than or equal to the predetermined threshold.

2. The integrated circuit of claim 1 further comprises a medical device that receives the radiation, wherein the radiation includes an ionizing radiation.

3. The integrated circuit of claim 2 further comprising an output module that outputs the indication to a system external to the integrated circuit wherein the indication indicates whether the medical device is sterilized.

4. The integrated circuit of claim 1 further comprising an output module that outputs the indication to a system generating the radiation wherein the system stops generating the radiation based on the indication.

5. The integrated circuit of claim 1 further comprising:
    a periodic activation module that activates the sensing module and the measuring module at predetermined time intervals; and
    an output module that outputs the amount of the radiation measured by the measuring module to an internal memory or a system with external memory that logs the amount of the radiation measured at the predetermined time intervals.

6. The integrated circuit of claim 1 wherein the sensing module includes a first oscillator having a first period that changes substantially due to the radiation and a second oscillator having a second period that does not change substantially due to the radiation, and wherein the measuring module measures the amount of the radiation based on a ratio of the first and second periods after the first and second oscillators are exposed to the radiation.

7. A method comprising:
- sensing radiation incident on an integrated circuit using a sensing element integrated in the integrated circuit, wherein the sensing element includes a MOSFET having a threshold voltage that shifts due to the radiation;
- measuring an amount of the radiation incident on the integrated circuit in response to sensing the radiation incident on the integrated circuit based on an amount of shift in the threshold voltage of the MOSFET after exposure to the radiation;
- comparing the measured amount of the radiation to a predetermined threshold; and
- generating an indication that the measured amount of the radiation is less than the predetermined threshold or that the measured amount of the radiation is greater than or equal to the predetermined threshold.

8. The method of claim 7 wherein the radiation includes an ionizing radiation, the method further comprising:
- outputting the indication to a system external to the integrated circuit; and
- determining based on the indication whether a medical device integrated in the integrated circuit is sterilized.

9. The method of claim 7 further comprising:
- outputting the indication to a system external to the integrated circuit; and
- determining based on the indication whether to continue or stop generating the radiation.

10. The method of claim 7 further comprising:
- measuring the radiation at predetermined time intervals; and
- logging the amount of the radiation measured at the predetermined time intervals.

11. The method of claim 7 wherein the sensing element comprises first and second oscillators respectively having first and second periods, the method further comprising measuring the amount of the radiation based on a ratio of the first and second periods after the first and second oscillators are exposed to the radiation, wherein the first period of the first oscillator changes substantially due to the radiation and the second period of the second oscillator does not change substantially due to the radiation.

* * * * *